United States Patent [19]
Singh et al.

[11] Patent Number: 6,160,019
[45] Date of Patent: *Dec. 12, 2000

[54] PARENTERAL WATER-MISCIBLE NON INTENSELY COLORED INJECTABLE COMPOSITION OF NON-STEROIDAL ANTI-INFLAMMATORY DRUGS

[75] Inventors: Amarjit Singh; Rajesh Jain, both of New Delhi, India

[73] Assignee: Panacea Biotec Limited

[ * ] Notice: This patent is subject to a terminal disclaimer.

[21] Appl. No.: 09/120,099

[22] Filed: Jul. 21, 1998

[30] Foreign Application Priority Data

Jan. 12, 1998 [IN] India .................................. 56/DEL/98

[51] Int. Cl.$^7$ ..................................................... A61K 31/18
[52] U.S. Cl. ...................... 514/605; 424/78.05; 424/449
[58] Field of Search ................................ 424/78.05, 449; 514/605

[56] References Cited

U.S. PATENT DOCUMENTS 5,688,829  11/1997  Jain et al. ................................. 514/605
5,716,609   2/1998  Jain et al. ............................. 424/78.05

FOREIGN PATENT DOCUMENTS

1389/DEL/95   7/1995  India .
2046/DEL/95  11/1995  India .
2047/DEL/95  11/1995  India .
2048/DEL/95  11/1995  India .

OTHER PUBLICATIONS

Daffonchio.L et al. Inflammatory Research 45: 259–264, 1995.

Primary Examiner—Howard C. Lee
Attorney, Agent, or Firm—Quarles & Brady LLP

[57] ABSTRACT

A Parenteral Water-miscible non-intensely colored injectable composition of Non-steroidal anti-inflammatory drugs is disclosed. The invention utilizes solubilization techniques to achieve sufficiently high concentrations of Nimesulide suitable to deliver therapeutic doses in conveniently small volumes using water and without any salt form or complexing agent of Nimesulide. In the composition of the invention all the ingredients of the base are hydrophillic. The hydrophillic base serves the advantage of better miscibility with body fluids, faster drug disposition and better compatibility with the tissue environment.

6 Claims, No Drawings

PARENTERAL WATER-MISCIBLE NON INTENSELY COLORED INJECTABLE COMPOSITION OF NON-STEROIDAL ANTI-INFLAMMATORY DRUGS

The present invention relates to novel therapeutic non-intensely colored, water miscible, injectable analgesic pharmaceutical compositions of non-steroidal anti-inflammatory drugs (NSAIDs) and a process for the manufacture of such drugs. The analgesic injectable composition is very useful in mammals particularly in humans for the treatment of acute painful conditions like post-operative trauma, pain associated with cancer, sports injuries, migraine headache, neurological pain and pain associated with sciatica and spondylitis. For these indications some modified route of administrations may also be construed.

BACKGROUND OF THE INVENTION

Non-steroidal anti-inflammatory drugs such as those belonging to the category of cyclo-oxygenase-2 inhibitors including Nimesulide are highly hydrophobic compounds and readily precipitate even in the presence of minor amounts of water.

It is therefore very difficult to formulate non-steroidal anti-inflammatory drugs which are inhibitors of cycle-oxygenase-2 as an injectable composition for intramuscular or intravenous use.

In the past, efforts have been made to make an injectable composition of Nimesulide.

An injectable formulation of Nimesulide has been reported in PCT Patent No. WO 95/34533 which discloses utilizing a salt form of Nimesulide with L-lysine which is in turn further complexed with cyclodextrins which may be dissolved in water to give an injectable preparation. The maximum solubility achieved by this injectable composition was reported to be 2.4 mg/ml which is not sufficient for intramuscular administration as it would require very large volumes to administer therapeutic doses. Moreover making a salt form of Nimesulide and then combining with Cyclodextrins not only makes the process cumbersome but also increases the cost of the formulations.

Another reference (Daffonchio, L. et al. Inflammatory Research 45: 259–264; 1995) wherein Nimesulide is dissolved in saline for intravenous administration for experimental studies in animals also describes only very dilute solutions which cannot deliver therapeutic doses in humans.

The disadvantages of WO 95/34533 and problems associated therewith were overcome by the invention described in U.S. Pat. No. 5,688,829 (Corresponding Korean Application No. 96-48013, Australian Application No. 67993/96 and Japanese Patent Application No. 8-290585, all pending) by the inventors of the present invention.

This invention utilizing solubilization techniques was able to achieve sufficiently high concentrations of Nimesulide suitable to deliver therapeutic doses in conveniently small volumes using a base which was oily in nature without using water and without any salt form or complexing agents of Nimesulide.

The present invention comprises a composition wherein all the ingredients of the base are hydrophilic. The hydrophilic base serves the advantage of better miscibility with body fluids, faster drug disposition and better compatibility with the tissue environment.

It is an objective of the present invention to provide an injectable analgesic hydrophilic composition of non-steroidal anti-inflammatory drugs which are non-intensely colored and have better miscibility with body fluids. The hydrophilic compositions described herein can be administered both intravenously and intramuscularly.

It is another objective of the present invention to provide a novel process for the preparation of a parenteral hydrophilic injectable composition of NSAIDs.

SUMMARY OF THE INVENTION

The invention comprises a novel injectable aqueous miscible composition of cyclo-oxygenase-2 inhibitors such as Nimesulide which comprises:

1. Cyclooxygenase inhibitors.
2. Alkyl amides/Alkyl sulphoxides or pyrrolidones.
3. Glycols.
4. 0 to 20% of water.

DETAILED DESCRIPTION OF THE INVENTION

The cyclo-oxygenase-2 inhibitors belonging to the category of NSAIDs are selected from the group comprising of Nimesulide, Nabumetone, and Flosulide and derivatives thereof.

The Alkyl amides/Alkyl sulphoxides or pyrrolidones in accordance with the present invention are selected from the group—Dimethylacetamide, Dimethylformamide and Dimethylsulphoxide or N-Methyl Pyrrolidone.

The glycols in accordance with the present invention are selected from the group Polyethylene Glycol MW 200 to 6000, Propylene Glycol, Hexylene glycols, Butylene glycols and Glycol derivatives such as Polyethylene Glycol 660 hydroxy stearate (commercially available as Solutrol HS15).

The composition may also comprise the following conventional additional ingredients—surfactants, hydrophilic polymers, solubility enhancing agents i.e. Glycerine, various grades of Polyethylene oxides, β-cyclodextrins like sulfo butyl ether-β-cyclodextrin, Transcutol and Glycofurol, tonicity adjusting agents, local anesthetics, pH adjusting agents and buffers.

Preferably, the non-steroidal anti-inflammatory drug belonging to the category of cyclooxygenase-2 inhibitors is Nimesulide and derivatives thereof and is present in the composition from 0.1 to 10% w/v.

More preferably, Nimesulide is present from 0.5 to 8% w/v.

Still more preferably, Nimesulide is present in the composition from 1.2 to 4.8% w/v. Preferably the composition in accordance with the present invention comprises Alkyl amides/Alkyl sulphoxides or pyrrolidones from 2.0% to 95% w/v.

More preferably, the composition comprises Alkyl amides/Alkyl sulphoxides or pyrrolidones from 5% to 90%.

Still more preferably, Alkyl amides/Alkyl sulphoxides or pyrrolidones are present from 10% to 20% w/v.

Preferably, Glycols are present in the composition from 0.1% to 95% w/v.

In a preferred embodiment of the invention, there is described an injectable, water miscible, non-intensely colored, analgesic pharmaceutical composition of Nimesulide which comprises:

| | |
|---|---|
| Nimesulide from | 0.1 to 10% w/v |
| Dimethylacetamide from | 2.0 to 90% w/v |
| Polyethylene Glycols from | 0.1 to 95% w/v, and |
| Water from | 0 to 20% w/v. |

In a preferred embodiment, the drug is dissolved in an oily phase and emulsified in aqueous phase using surfactants including lecithins to yield a microemulsion or emulsion suitable for intravenous use.

In accordance with the present invention there is also described a novel process for the manufacture of an injectable, water miscible, analgesic pharmaceutical composition of an NSAID.

The process comprises:

a) Dissolving Nimesulide in Dimethylacetamide and adding thereto freshly distilled Benzyl Alcohol and stirring. Adding Polyethylene Glycol 400 to the above solution and mixing. Slowly adding Hydrochloric Acid to the solution with stirring, and then adding Propylene Glycol to the solution so that the volume of the solution is brought up to 95% of the actual batch size. The solution thus formed should have a pH between 2.0 to 3.0. If it is not in this range, then it can be adjusted to this range either with Sodium Hydroxide (10% w/v solution) or a Hydrochloric Acid solution. Propylene Glycol is then added until the final volume is reached.

b) Filter the resultant solution through 0.45 micron nylon membrane filter using a 6 micron glass fiber pre-filter. Collect the filtered solution in a clean fiber-free vessel. Fill fiber-free sterile 2 ml amber USP Type 1 glass ampoules with the solution with pre and post filling nitrogen flushing.

c) Sterilize the ampoules by autoclaving. Optically inspect all the ampoules and after release by Quality Control Department, and label the good ones.

The invention will now be described by the following examples of injectable analgesic compositions of NSAIDs.

EXAMPLE 1

| | % w/v |
|---|---|
| Nimesulide | 2% |
| Dimethylacetamide | 10% |
| Water | 1% |
| Benzyl Alcohol | 4% |
| BHA (Butylated Hydroxy Anisole) | 0.1% |
| Polyethylene Glycol 300 | q.s. to 100% |

EXAMPLE 2

| | % w/v |
|---|---|
| Flosulide | 1% |
| N-methyl pyrrolidone | 5% |
| Dimethylacetamide | 5% |
| Polyethylene Glycol 400 | 30% |
| Water | 5% |
| Benzyl Alcohol | 2% |
| a-tocopheryl acetate | 0.05 |
| Propylene Glycol | q.s. - 100% |

EXAMPLE 3

| | % w/v |
|---|---|
| Nimesulide | 1.2% |
| Dimethylacetamide | 10% |
| Benzyl Alcohol | 4% |
| Propylene Glycol | q.s. - 100% |

EXAMPLE 4

| | % w/v |
|---|---|
| Nimesulide | 10% |
| Benzyl Alcohol | 2% |
| Dimethylacetamide | q.s. - 100% |

EXAMPLE 5

| | % w/v |
|---|---|
| Nimesulide | 0.5% |
| Benzyl Alcohol | 2% |
| Lecithin (Lipoid E-80) | 1% |
| Dimethylacetamide | 10% |
| Water | 2% |
| Polyethylene Glycol 300 | q.s. - 100% |

On affecting Acute Toxicity studies on Balb/C Mice by intraperitoneal route, the $LD_{50}$ was found to be 160 mg/kg, $ED_{50}$=3 mg/kg with therapeutic index=53.3 in mice. This demonstrates high safety of the present invention. In preliminary animal trials and in preclinical trials, the injectable analgesic composition according to the present invention was shown to possess marked analgesic activity. Further, it has been found to non-toxic even on repeated applications to the same site.

No incidence of tissue necrosis or any other side effect was observed. The analgesic dose ranged from 0.1 mg/kg to 8.4 mg/kg.

Since many apparently different embodiments of the present invention could be made without departing from the spirit and scope thereof, it is intended that the description of the invention herein be interpreted as being illustrative only and not limiting in any manner whatsoever.

We claim:

1. A process for the manufacture of parenteral, water-miscible, injectable nimesulide composition which comprises the steps of:

(1) dissolving 0.1 to 10% w/v of nimesulide in 2 to 90% w/v of dimethylacetamide to form a solution;
(2) adding benzyl alcohol to the solution of step (1) while
(3) adding 0.1 to 60% w/v of polyethylene glycol to the solution of step (2);
(4) adding hydrochloric acid to the solution of step (3); and
(5) adding propylene glycol to the solution of step (4).

2. The process of claim 1 wherein step (1) comprises dissolving 0.25% to 10% w/v of nimesulide in 2 to 90% w/v of dimethylacetamide to form a solution.

3. The process of claim 1, further comprising a step of adjusting the solution of step 5 to a pH of between 2 to 3.

4. The process of claim 1, further comprising a step of filtering the solution of step 5.

5. The process of claim 1, further comprising a step of placing the solution of step 5 into a suitable container.

6. The process of claim 1, further comprising a step of sterilizing the solution of step 5.

* * * * *